US012263021B2

(12) United States Patent
Hei et al.

(10) Patent No.: US 12,263,021 B2
(45) Date of Patent: Apr. 1, 2025

(54) GLUCOSE MONITORING METHOD AND SYSTEM

(71) Applicant: University of Louisiana at Lafayette, Lafayette, LA (US)

(72) Inventors: Xiali Hei, Lafayette, LA (US); Yazhou Tu, Lafayette, LA (US)

(73) Assignee: University of Louisiana at Lafayette, Lafayette, LA (US)

( * ) Notice: Subject to any disclaimer, the term of this patent is extended or adjusted under 35 U.S.C. 154(b) by 963 days.

(21) Appl. No.: 16/952,692

(22) Filed: Nov. 19, 2020

(65) Prior Publication Data

US 2021/0145370 A1  May 20, 2021

Related U.S. Application Data

(60) Provisional application No. 62/937,319, filed on Nov. 19, 2019.

(51) Int. Cl.
 *A61B 5/00* (2006.01)
 *A61B 5/11* (2006.01)
 *A61B 5/145* (2006.01)

(52) U.S. Cl.
 CPC ........... *A61B 5/746* (2013.01); *A61B 5/11* (2013.01); *A61B 5/14532* (2013.01); *A61B 5/4806* (2013.01); *A61B 5/681* (2013.01); *A61B 5/6887* (2013.01); *A61B 5/725* (2013.01); *A61B 2562/0219* (2013.01); *A61B 2562/0247* (2013.01)

(58) Field of Classification Search
 CPC ....... A61B 5/746; A61B 5/11; A61B 5/14532; A61B 5/4806; A61B 5/681; A61B 5/6887; A61B 5/725; A61B 2562/0219; A61B 2562/0247
 See application file for complete search history.

(56) References Cited

U.S. PATENT DOCUMENTS

| | | | | |
|---|---|---|---|---|
| 2011/0105873 | A1* | 5/2011 | Feldman | A61B 5/14546 600/365 |
| 2017/0031449 | A1* | 2/2017 | Karsten | G06Q 10/1095 |
| 2017/0273607 | A1* | 9/2017 | Facchinetti | G16H 50/50 |
| 2018/0277246 | A1* | 9/2018 | Zhong | A61B 5/746 |

* cited by examiner

*Primary Examiner* — Christian Jang
(74) *Attorney, Agent, or Firm* — Kean Miller LLP; Lauren J. Rucinski; Jessica C. Engler

(57) ABSTRACT

This invention provides a system and method to protect an artificial pancreas' sensor, infusion system, and alert systems from EMI/wireless attacks using a medical software or application, close the gap between sensor glucose and blood glucose, and build a non-invasive hypoglycemia and hyperglycemia false alarm detection scheme with the help of a wristband. This inventive method and system provides a more accurate blood glucose prediction. It comprises preprocessing the CGM readings with Kalman smoothing for sensor error correction improves the robustness of the BG prediction. In one or more embodiments, the inventive system and method uses one or more physiological information such as meal, insulin, aggregations of step count, and preprocessed CGM data. The invention provides a novel approach for leveraging the stacked LSTM based deep RNN model to improve the BG prediction accuracy. The invention provides a special circuits-Transduction Shield- to detect and correct the sensor errors caused by EMI attacks.

7 Claims, 13 Drawing Sheets

GLUCOSE MONITORING METHOD AND SYSTEM

CROSS REFERENCE TO RELATED APPLICATIONS

This application claims priority to the PROVISIONAL U.S. patent application No. 62/937,319 entitled DIABETES DETECTION SYSTEM, filed Nov. 19, 2019.

STATEMENT REGARDING FEDERALLY SPONSORED RESEARCH OR DEVELOPMENT

Not Applicable.

REFERENCE TO A "SEQUENCE LISTING," A TABLE, OR A COMPUTER PROGRAM

Not Applicable.

SUMMARY OF THE INVENTION

This invention provides a system and method to protect an artificial pancreas system's glucose sensor, infusion system, alert and control systems from EMI/Wireless interference or "attacks" using a medical software or application, to close the gap between sensor glucose and blood glucose, and to build a non-invasive hypoglycemia and hyperglycemia false alarm detection scheme with the help of a wristband.

This invention provides a novel method to detect/predict the real hypoglycemia and hyperglycemia cases by monitoring the patient's physiological data such as heart rate, galvanic skin response, food eaten, and exercise steps to help detect the sensor glucose alert manipulating attacks without missing life-threatening cases. Preprocessing the CGM readings with Kalman smoothing for sensor error correction improves the robustness of the BG prediction.

The invention provides a novel approach for leveraging the stacked LSTM based deep RNN model to improve the BG prediction accuracy.

The invention provides continuous logging and analyzing of the user's behaviors (e.g., exercise, stress, frequently drinking water, etc.), which is of particular concern in the prediction and therapy of diabetes.

In one or more embodiments, the inventive system and method uses one or more physiological information such as meal, insulin, aggregations of step count, and preprocessed CGM data.

DESCRIPTION OF THE DRAWINGS

The drawings constitute a part of this specification and include exemplary embodiments of the DIABETES DETECTION SYSTEM, which may be embodied in various forms. It is to be understood that in some instances, various aspects of the invention may be shown exaggerated or enlarged to facilitate an understanding of the invention. Therefore, the drawings may not be to scale.

BACKGROUND

Figure 1:
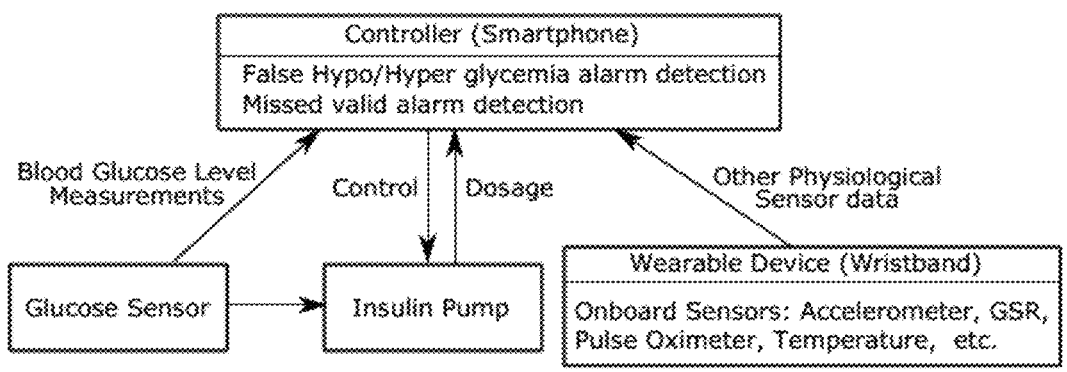
FIG. 1 is an illustration of the structure of the false/missed hypoglycemia and hyperglycemia alarm detection system.

Diabetes Mellitus is a chronic disorder associated with abnormally high levels of blood glucose because the body is unable to produce enough insulin to meet its needs. α-cell and β-cell in the pancreas are responsible for maintaining the glucose level in blood by secreting insulin and glucagon hormones. Diabetes can be classified primarily into two categories. Type-1 diabetes is due to β-cell destruction and would cause absolute insulin deficiency. Type-2 diabetes is due to a progressive insulin secretory defect on the background of insulin resistance. In type-1 diabetes, hypoglycemia sets in when blood sugar levels are too low (blood glucose concentration<70 mg/dl) and hyperglycemia occurs when blood sugar levels are too high for a prolonged period (blood glucose concentration>180 mg/dl). In the long term, hyperglycemia causes severe complications of heart, blood vessel, eyes, kidneys, and other organs. Therefore, proper diabetes management is vital for human health.

More than 100 million U.S. adults are now living with diabetes or prediabetes, according to a report released by the Centers for Disease Control and Prevention (CDC). As of 2017, 30.3 million Americans have diabetes. External insulin treatments are indispensable for T1D diabetes patients to maintain the blood glucose level in a healthy range. With the naive approach for diabetes management, a patient needs to measure BG concentration several times throughout the day and night using the finger-stick test. Currently, it is the most common self-monitoring approach. Improved techniques such as a combination of an insulin pump for Continuous Subcutaneous Insulin Infusion (CSII) and a device for continuous glucose monitoring (CGM), are required for an effective blood glucose management system, known as sensor-augmented-pump (SAP) therapy. CGM device takes glucose measurements with an interval of a particular timeframe. For example, most of the CGM devices take 288 measurements per day with five minutes interval. SAP therapy has been further improved by utilizing control algorithms for dynamic insulin delivery. In terminology, that is known as "Artificial Pancreas" (AP), closed-loop control of blood glucose in diabetes. Statistical and machine learning techniques with the availability of previous continuous BG records make BG prediction more convenient. This prediction mechanism allows a patient or control algorithm to take the initiative to lower the adverse effect of unintended glycemic events.

More than 550,000 patients use insulin pumps. AP systems, including a glucose sensor, may be used for the treatment of Type 1 diabetes.

The main components of an AP as defined by the FDA are: (1) a continuous glucose monitor (CGM) with a sensor; (2) a control algorithm to link blood glucose levels with insulin delivery, which can be run on any number of devices including an insulin pump, a computer or a smartphone; (3) an automatic insulin delivery system—pump; and (4) the patient. In the treatment of Type 1 diabetes, an AP has more advantages than conventional pumps due to its closed-loop control system that automatically adjusts the insulin delivery rate based on the continuous feedback from the glucose sensor.

Just like any device connected to the internet of things, an AP is vulnerable to third party interference through its wireless connection, or "attacks." These attacks may be inadvertent or purposeful. There are several existing wireless attacks on certain models of wireless insulin pumps, such as Medtronic MiniMed 722 and Animas OneTouch Ping. Wireless attacks could cause a vulnerable blood glucose management device to get inaccurate readings by jamming, or to order a pump to dose insulin by exploiting its plaintext communication. Such attacks could control vulnerable insulin pumps' operations to deliver fatal doses (e.g., 300 units of insulin) with a wireless USB device. In fact, third parties or "adversaries" could manipulate the measurement of a Dexcom G5 glucose sensor by electromagnetic interference (EMI) signal injection.

Figure 2:
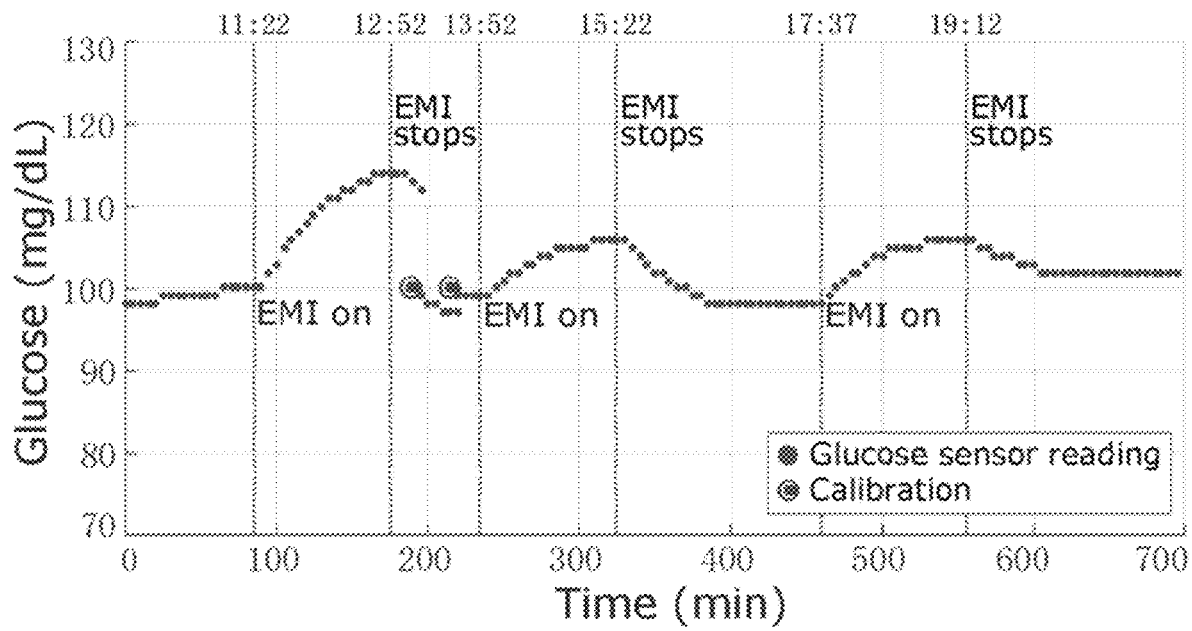
FIG. 2 shows the result of the EMI attack experiment on a Dexcom G5 glucose sensor. Before the attack, the sensor reading was stabilized at around 100 mg/dl for over an hour. With attacks, the glucose measurement was increased, which could trick an AP system to overdose.

FIG. 2 shows the result of the EMI attack experiment on a Dexcom G5 glucose sensor. Before the attack, the sensor reading was stabilized at around 100 mg/dl for over an hour. With attacks, the glucose measurement was increased, which could trick an AP system to overdose.

Additionally, pressure sensors are widely used for occlusion detection in medical infusion pumps. Pressure sensors can be susceptible to EMI rectification. A compromised pressure sensor might suppress a valid alert or induce a faked infusion blocked alert, creating safety and usability issues. The pattern of the clock signal of a micro-controller could also be manipulated by exploiting the working principle of the crystal oscillator. The clock signal could be slowed down or sped up by 25%, and attenuated or amplified using intentional EMI signals and resonant acoustic signals. For insulin pumps, a compromised clock signal could lead to unexpected control signals and a consequent manipulated injection rate that is unsafe for the patient.

The effect of the above attacks put the patient at risk. Even though FDA guidelines recommend that medical device manufacturers remain vigilant about cybersecurity issues and take responsible steps to protect patients from potential risks, most of the currently available commercial medical devices do not have enough security mechanisms embedded in the hard/software because of the high cost and potential regulatory requirements. Also, it is difficult to replace or update all the instances of a product in the market even if a vulnerability has been found; these medical devices could take years to be replaced by newer models.

Thus, it is essential to investigate the root cause of false alarms and propose methods to identify the real hypoglycemia and hyperglycemia events. Such methods are useful for early diagnoses of diabetes before the poor blood glucose control harms the patient's organs.

Over the past decade, some research has been carried out to secure medical devices. MedMon is a general framework for securing medical devices based on wireless channel monitoring and coarse-grained anomaly detection. SecureVibe consists of a secure acoustic channel that allows encrypted messages to be periodically sent between the device and an external station with high energy efficiency. Martin et al. fully reverse-engineered the wireless communication protocol among all the peripherals of the insulin pump system.

However, these and other existing solutions for wireless insulin pumps still suffer from the following limitations. First, some have low usability because they require the patient to carry extra devices beyond a smartphone and wristband. Second, many of them cannot protect against the physical signal injection attacks at extremely low-end devices such as sensors and transmitters. None could protect the closed-loop control of the AP systems from cyberphysical attacks. For example, the scheme proposed in some systems cannot be applied to defend against glucose sensor attacks because they use finger-stick data, not suitable for the automatic sensing in an AP system.

This invention addresses those issues by providing a system and method to protect the AP's sensor, infusion system, alert systems from attacks using a medical software or application, close the gap between sensor glucose and blood glucose, and build a non-invasive hypoglycemia and hyperglycemia false alarm detection scheme with the help of a wristband. The structure of one embodiment of the system is illustrated in FIG. 1. The inventive system and method uses a non-invasive wristband to detect the real hyperglycemia and hypoglycemia events for diabetes and pre-diabetes by developing the hardware prototype and software modules.

Various statistical and machine learning methodologies have been proposed for blood glucose forecasting. The autoregressive integrated moving average (ARIMA) model-based algorithm is an example of a classical statistical method for blood glucose prediction. The primary limitation of naive machine learning approaches is that it fundamentally depends on the representation of the input data (e.g., support vector regression or k-nearest neighbor classifier). Prior art has proposed a generic physiological model of blood glucose dynamics to generate essential features of a Support Vector Regression (SVR) model that took daily events such as insulin boluses and meals into consideration. The meal model, insulin model, and exercise model were used with the SVR model in work.

Several prior art works have been done for blood glucose prediction using artificial neural networks (ANNs). Classically, an ANN has a single hidden layer. However, deep learning models have many hidden layers. These deep models with higher complexity outperform traditional shallow neural networks. These deep learning models with higher complexity can learn the pattern automatically from data. Especially for sequential data, recurrent neural networks (RNNs) outperform feed-forward ANNs. However, the drawbacks of using classical RNNs are limitations in its ability to discover, that arises from the vanishing/exploding gradient problem. This issue has been addressed by Long short-term memory (LSTM) networks with the addition of memory cell and forget gate to classical RNN. In some prior art, convolutional RNN and LSTM are investigated for BG prediction more accurately. For instances, prior art has used RNN with Gated Recurrent Unit (GRU) cell and Bi-LSTM based RNN for BG forecasting. However, the accuracy achieved with state-of-the-art models for real patient data is not high enough that these approaches might not be applicable in the health domain. For example, the best average RMSE value achieved for the OhioT1DM dataset is 19.04 mg/dl so far in the most recent works. Moreover, in these recently proposed methodologies with the RNN model, sensor fault is not taken into consideration. This inventive method and system addresses the deficiencies in the prior art, including the relatively low accuracy in the BG prediction schemes. The invention provides an improvement to the reliability and accuracy of the BG forecasting mechanism.

Early detection and prevention of potential glycemic events such as hypoglycemia and hyperglycemia are one of the primary purposes of the artificial pancreas system. Comparatively, more extended works have been done in the prior art associated with hypoglycemia detection than the detection of hyperglycemic events. Several statistical methods were studied, such as linear prediction models, recursive auto-regressive partial least squares models and multi-variable model, for modeling the CGM sensor data for a reliable hypoglycemia early alarm system. In some prior art, an RNN model and two different autoregressive models were proposed to design a hypoglycemia/hyperglycemia early warning system (EWS). It developed a time-sensitive ANN-based hypoglycemia prediction system that can predict future hypoglycemic events within a prediction horizon (PH) of 30 minutes. Additional physiological models, along with ANN, are studied in other prior art to predict nocturnal hypoglycemia. However, there is highly limited to no prior art works explicitly for the detection of hyperglycemia. Accordingly, this invention provides a method and system which demonstrates that the electrocardiographic (ECG) signals can be employed with the ANN model to detect hyperglycemic events practically and non-invasively.

CGM sensor reading is a crucial factor in BG prediction as a slight error in CGM sensor reading might result in the wrong prediction. However, sensor fault is very common in the CGM system. That is why most of the clinical BG data sets are prone to have errors. Several factors are responsible for that kind of fault, such as the decay of sensor sensitivity, pressure-induced sensor attenuation (PISA), and interruption in signal transmission, etc. Furthermore, bias and latency might be present in a CGM reading. Another issue is that the reading of sensors from the same manufacturer might be different due to manufacturing variability. As a consequence, the predicted BG value and the estimation for insulin might be erroneous due to such faulty BG reading. Consequently, it might decrease the efficacy of the diabetes management system. So, to propose more reliable BG forecasting methodologies, sensor fault should be taken into consideration. However, synthesized data sets are exceptions of this case as this is out of the scope of the sensor fault.

Moreover, there might be another issue responsible for inaccurate BG prediction. The CGM sensor glucose is measured from interstitial fluid samples instead of the blood sample. However, there is a discrepancy in time and magnitude between BG and interstitial glucose (IG). In the BG forecasting system, CGM sensor readings are used as one of the primary inputs to predict the future BG level. As IG and BG values are different, the BG prediction with IG as input is challenging. The inventive system and method provides BG prediction made with the Kalman smoothed CGM reading. This method provides a reading that is closer to actual BG reading measured with fingerstick than the prediction made with unprocessed CGM reading.

In one or more embodiments, this inventive method and system provides more accurate and reliable forecasting accuracy in terms of RMSE. In one or more embodiments it provides a novel approach using a stacked LSTM based deep recurrent neural network architecture for BG prediction. In one or more embodiments, it provides a more reliable BG prediction system by utilizing Kalman smoothing for mitigating the sensor fault in CGM reading. In one or more embodiments, it provides a method for improving BG predication accuracy that comprises a person's step count information from a fitness band.

DETAILED DESCRIPTION

The subject matter of the present invention is described with specificity herein to meet statutory requirements. However, the description itself is not intended to necessarily limit the scope of claims.

Current glucose sensors suffer from an approximately 10% error rate in their measurements, which could cause false alarms in certain scenarios. Moreover, cyber-physical attacks on sensors could intentionally induce an AP to give more false alarms or suppress valid alarms.

To address these issues, this inventive system and method provides a novel approach to detect the real hypoglycemia and hyperglycemia cases by monitoring the patient's physiological data such as heart rate, blood oxygen saturation, galvanic skin response, and exercise steps to help detect the sensor glucose alert manipulating attacks without missing life-threatening cases.

The system implements various glucose prediction algorithms on the test-bed in order to detect the deviation of the measured glucose and the predicted glucose. The resulting hardware and software developments will help researchers and medical manufacturers to mitigate the gap between the patients' sensor glucose and blood glucose. After predicting the glucose correctly, the predicted glucose and the sensor glucose are compared and checked to determine whether the attacks are existing and the hypoglycemia/hyperglycemia alerts are real. Also, the system and method may identify the glucose sensor errors or EMI attacks before poorly controlled blood glucose induces adverse effects in the patient's organs or overall health.

Additionally, an adversary who can compromise a single sensor may cause system-wide malfunctions in internet of things devices. Previously, many schemes were based on redundant sensors. Thus, this inventive system and method provides a protection scheme based on redundant circuits called a transduction shield (TS), which forms a basic unit in the sensor processing circuits.

The system and method provides an integrated approach including software check and hardware protection, which could be ideally integrated with other insulin dosage control systems. Further, it provides a mechanism to aid a patient in achieving higher glucose control and decreased frequency of hypoglycemia and hyperglycemia events.

This invention also provides a deep learning approach for blood glucose prediction using a multi-layered LSTM based recurrent neural network model. In the example, it uses the OhioT1DM dataset, containing eight weeks' data for each of six people with type-1 diabetes, for training and evaluation of the proposed model. It uses several features instead of only CGM measurement. This is because the dynamics of the glucoregulatory system depend on several factors such as carbohydrate intake from meals, the amount of bolus dose or infused insulin, exercise, and physical activeness. Using only the CGM measurement as input might not be enough for learning those complex dynamics. Therefore, the method provides several combinations of different physiological information from the OhioT1DM dataset to choose the most optimal combination of those for the proposed model. The example shows that step count information from a fitness band can be a useful feature.

This invention provides in one embodiments for the use of the combination of CGM reading, step count, carbohydrate intake from the meal, and bolus dose, is the most optimal feature set as the input of the model.

Figure 3:
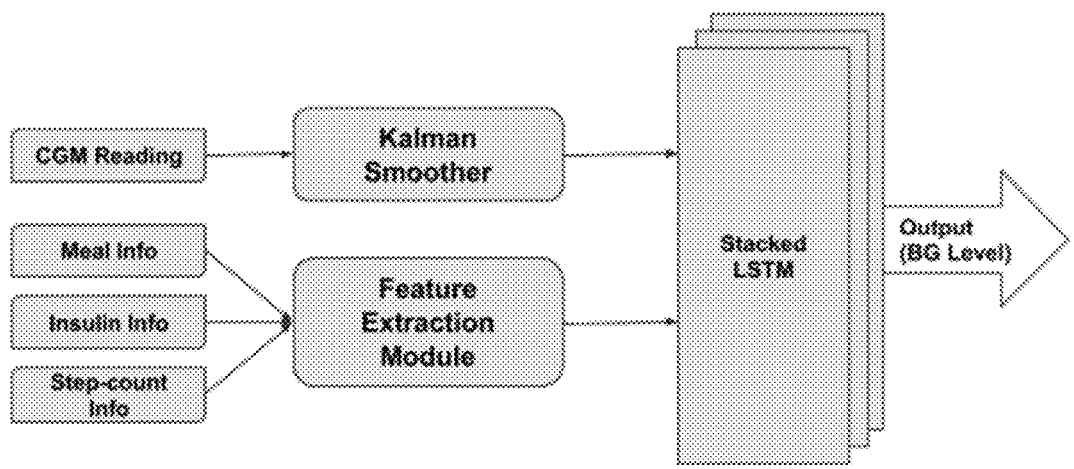
FIG. 3 shows the flow charts of one embodiment of the glucose prediction scheme.

The example uses preprocessed CGM data with Kalman smoothing (KS) instead of using raw CGM data to mitigate the effect of sensor fault on BG prediction. The overall architecture of the inventive BG prediction system has been illustrated in FIGS. 3 and 13.

The insulin pump is the key element of an AP system. However, the frequency of the pump's central processing unit (CPU) is relatively slow and the memory is limited, e.g. Minimed 723's CPU is only 20 Mhz with a Flash memory of 64K and a RAM of 2K. Thus, it is not practical to run all false alarm detection algorithms in the insulin pump itself. Because a smartphone has become a basic personal digital assistant (PDA) for almost everyone, in one or more embodiments, the smartphone runs the control algorithms and communicates with the pump.

Smartphones also offer the ability to integrate an applicable app into the system and method. For instance, an open-source automated insulin delivery app—known as Tidepool Loop®—is under the review by FDA.

Much prior art requires offline learning to obtain the infusion pattern of an insulin pump. Whereas the novel method here comprises a new online secure framework for the AP system. The framework includes two design modules: 1) online false hypoglycemia and hyperglycemia alarm detection system; 2) a robust glucose prediction system; and 3) an EMI attack detection and correction circuit and algorithms.

The inventive system and method makes the following key contributions: (1) design of a glucose prediction algorithm; (2) design of a special circuit for EMI attack detection and correction to protect the glucose sensor and pressure sensor in the wireless insulin pump system; (3) provision of physiological data-based life-threatening case like hypoglycemia checking.

The output of the glucose sensor plays a vital role in the AP system. For instance, a low sensor glucose value will stop the pump. If an adversary sends a super low SG reading to stop the pump, the patient cannot get necessary insulin and will be at risk of getting hyperglycemia. For instance, when the forged sensor data sent by an attacker is extremely low (i.e. less than 60), the AP will stop the infusion and issue a low sensor glucose (SG) alert. With current methods, the patient is required to respond to this type of alarm immediately with a fingerstick result. If the patient cannot conduct a fingerstick, the pump stops, cutting off necessary insulin. Also, if the patient must respond to several such alerts during sleeping hours, the patient will be exhausted. Similarly, an attacker could suppress low-SG alerts with equally undesirable results.

Thus, this system reduces false low-SG alerts without missing any life-threatening alerts. Prior art has proposed a classification procedure based on the AdaBoost algorithm with a rejection option to reduce false peripheral capillary oxygen saturation ($SpO_2$) alarms. However, the novel system incorporates SG rather than $SPO_2$. SG over 24 hours has more significant fluctuation than $SpO_2$. Furthermore, the inventive system is capable of detecting the false super low-SG alerts that could intentionally cause a denial of services (DoS) effect in AP systems.

The novel system and method comprises a false SG-alert detection model. The main observation is that a patient's physiological signals will change when he/she has hypoglycemia. Typically, the heart rate (HR) and galvanic skin response (GSR) rises with hypoglycemia or exercise. The skin tremor (TR) measured by an accelerator increases with hypoglycemia as well. The heart rate variety (HRV) decreases for actual (vs. false) hypoglycemia. In sum, heart rate and galvanic skin response are correlated with real hyperglycemia and hypoglycemia. The heart rate HR and galvanic skin response GSR are correlated with real hyperglycemia and hypoglycemia (hypo) events. Thus, the patient's vital signals like HR and GSR can be used to identify the faked SG-alerts and find suppressed SG-alerts with a high success rate. The novel system comprises monitoring one or more of the HR, HRV, GSR, and TR.

As part of the novel system, a patient's routine activities like sleeping, exercising, eating, and stress may be monitored. In one or more embodiments, the monitoring is performed on a smartphone or smart wearable device. In one or more embodiments, the system comprises sensors in a patient's wristband (for example, an Empatica E4 EDA/GSR Wristband) or a smartwatch to assist in attack detection.

In one or more embodiments, when there is a low-SG alert, the system checks the patient's physiological signals and activities data in the past 30-minutes or 60-minutes window to verify whether it is a valid alert. If it is a valid alert, the system issues the alarm. Otherwise, the system will categorize it as a false low-SG alert and suppress the alarm.

The system may also comprise a model to detect suspicious low-SG alerts. The inputs are: predicted glucose, sensor glucose, threshold. The output is a confidence score S. If the calculated confidence score S<Th, the alert event is labeled as a suspicious low-SG/high-SG alert, i.e., a possible low/high SG-alert manipulating attack. Otherwise, the alert event is labeled as valid. Through continuous monitoring and sending the patient out-of-band alerts, the possibility of missing a life-threatening case will be lowered.

To detect the false alerts of hypoglycemia and hyperglycemia, the following steps may be performed: first calculate/predict the glucose level according to the data obtained and then analyze the machine learning based method to predict the glucose.

Blood glucose (BG) management is crucial for type-1 diabetes patients resulting in the necessity of reliable artificial pancreas or insulin infusion systems. In recent years, deep learning techniques have been utilized for a more accurate BG level prediction system. However, continuous glucose monitoring (CGM) readings are susceptible to sensor errors. As a result, inaccurate CGM readings would affect BG prediction and make it unreliable, even if the most optimal machine learning model is used.

Thus, this inventive method and system provides a novel approach to predicting blood glucose level with a stacked Long short-term memory (LSTM) based deep recurrent neural network (RNN) model considering sensor fault.

In one or more embodiments, the Kalman smoothing technique for the correction of the inaccurate CGM readings due to sensor error is used. For the OhioT1DM dataset, containing eight weeks' data from six different patients, the average RMSE of 6.45 and 17.24 mg/dl for 30 minutes and 60 minutes of prediction horizon (PH), respectively can be seen with the inventive method and system. This is the leading average prediction accuracy for the ohioT1DM dataset.

Different physiological information, e.g., Kalman smoothed CGM data, carbohydrates from the meal, bolus insulin, and cumulative step counts in a fixed time interval, are crafted to represent meaningful features used as input to the model. The goal of the approach is to lower the difference between the predicted CGM values and the fingerstick blood glucose readings—the ground truth. The results indicate that the proposed approach is feasible for more reliable BG forecasting that might improve the performance of the artificial pancreas and insulin infusion system for T1D diabetes management.

Table 1 shows the average Root Mean Squared Error (RMSE) of the current model compared to three prior art.

TABLE 1

| Patient ID | Average RMSE of Model with Kalman Smoothed CGM | Average RMSE of Model with Raw CGM | Average RMSE of Prior Art 1 | Average RMSE of Prior Art 2 | Average RMSE of Prior Art 3 |
|---|---|---|---|---|---|
| 1 | 5.15 | 17.89 | 18.78 | 22.48 | 19.5 |
| 2 | 5.58 | 19.02 | 18.12 | 20.35 | 19 |
| 3 | 5.45 | 15.93 | 15.46 | 18.26 | 16.4 |
| 4 | 9.06 | 20.94 | 22.83 | 25.65 | 24.8 |
| 5 | 5.77 | 18.09 | 17.72 | 21.69 | 19.3 |
| 6 | 7.89 | 20.32 | 21.34 | 24.59 | 25.4 |
| Avg. | 6.48 | 18.70 | 19.04 | 22.17 | 20.73 |

In one or more embodiments, the system uses a filter to reconcile the sensor errors first, then uses artificial neural network (ANN) to predict the G[n]. Through this method, the average prediction errors are lowered. For example, the average prediction errors is 5 mg/dl for six patients in 8 weeks and after using Kalman filter smoothing, the predicted sensor glucose is more close to blood glucose and the average prediction errors could be lowered to 5 mg/dl.

Due to the increase of the prediction accuracy, the glucose error threshold can be more easily set to be 6 mg/dl, if the difference between the predicted glucose level and sensor glucose is greater than the threshold, this indicates an attack or error happening. Otherwise, the error is within the margin.

Example 1

The hardware-based anomaly detector discussed below would also be implemented to counter the EMI attacks at glucose sensor and pressure sensor in the AP system.

In order to provide more security for the glucose sensor, the system may comprise a hardware-based anomaly detector to counter the EMI attacks. To ensure the security and usability of sensor-based applications and systems, a defense approach that can be applied to different kinds of sensors is investigated herein. The underlying problem and challenge related to the data integrity issue of sensors under the effect of EMI is analyzed.

Sensors measure physical properties of an environment by transducing certain physical stimulus to electrical signals in circuits. However, under the effect of EMI, illegitimate signals can be induced in the analog circuits and imposed on the original signal. By exploiting non-linear effects, an adversary can transform EMI signals to in-band signals to manipulate the sensor output and deceive the system.

From the perspective of the system, only the transformed in-band signals will be observed. It is usually not easy for the system to detect, distinguish, and correct the corrupted sensor output especially when the sensor is subject to intentional manipulation of adversaries.

Figure 7:
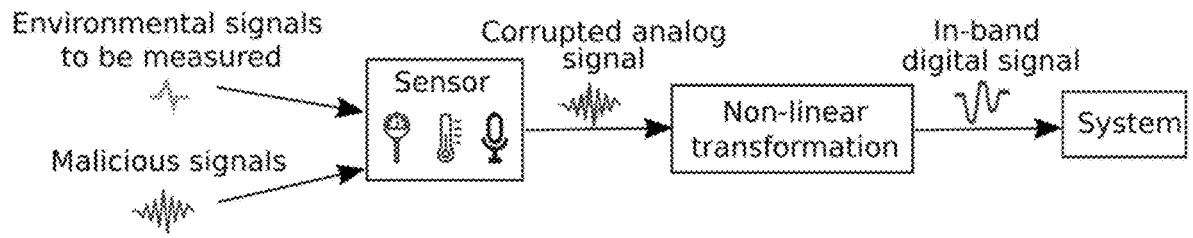
FIG. 7 illustrates the attack effects of EMI on sensors. Adversaries can exploit the non-linear analog sensor components to transform high-frequency EMI signals and manipulate the output. The system cannot distinguish the corrupted signal easily because both legitimate signals and malicious signals are in-band and the behavior of both signal sources are not completely predictable.

FIG. 7 illustrates the attack effects of EMI on sensors. Adversaries can exploit the non-linear analog sensor components to transform high-frequency EMI signals and manipulate the output. The system cannot distinguish the corrupted signal easily because both legitimate signals and malicious signals are in-band and the behavior of both signal sources are not completely predictable. Since both the environmental signal source and the malicious signal source are not completely predictable, it is difficult to detect or correct the corrupted signal.

The non-linearity of the circuits is another cause of the uncertainty since it transforms the out-of-band malicious signals into in-band signals and such non-linear transformation of real-world circuits are often too complex to predict or model accurately.

Sensor redundancy and sensor fusion based approaches could be used to detect anomaly or to gain more resilience when the system is subject to interference. However, the aforementioned uncertainty of the signals can fundamentally limit the performance of such approaches since multiple sensor are still subject to the effects of both the environmental signals and malicious signals (FIG. 7). Adversaries could attempt to affect multiple sensors at the same time. Moreover, it can be difficult to determine which sensors are corrupted when their measurements are conflicted.

It can be challenging to eliminate the susceptibility of the circuits to intentional EMI especially since adversaries can try to use different carrier frequencies to affect the sensor.

This inventive method and system provides a transduction shield (TS) as a general approach to protect the security and usability of sensors and automated processes in the presence of EMI. In this inventive approach, the effects of EMI are not sought to be eliminated, since complete elimination of the EMI is difficult and could cause design challenges for system designers.

Figure 8:
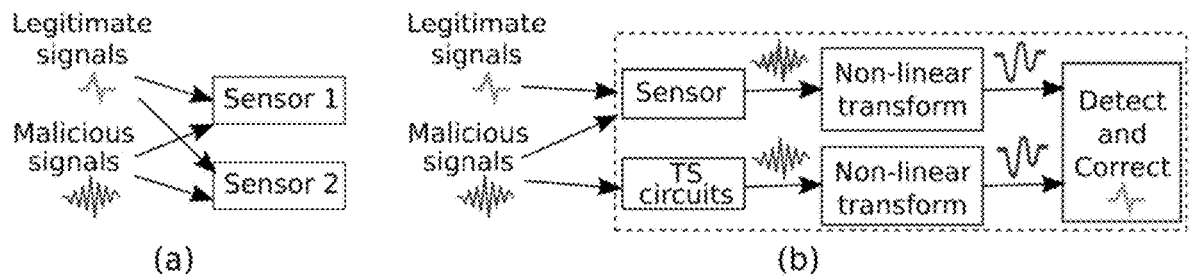
FIG. 8 shows how the malicious EMI signals would be captured by the transduction shield (TS) circuits.
Figure 10:
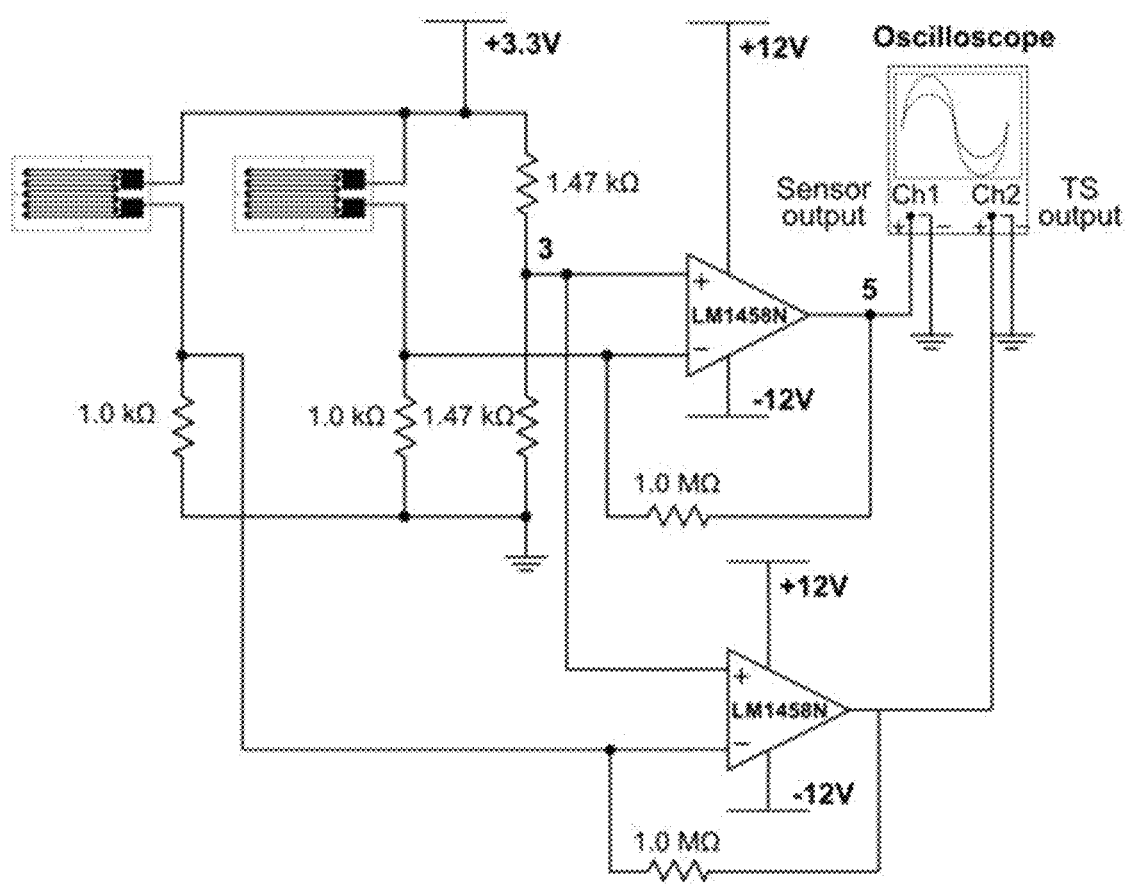
FIG. 10 shows the diagram of one example of transduction shield circuits.

In other embodiments, this inventive method and system integrates a transduction-aware circuit to harness the vulnerabilities. In this embodiment, the circuit of the transduction shield shares the same vulnerabilities as the sensor to be protected. However, the circuit is also insensitive to the environmental signals that the sensor is intended to measure. FIG. 10 shows the diagram of one example of transduction shield circuits As illustrated in FIG. 8, the malicious signals would be captured by the TS circuits. To the left of FIG. 8, in sensor redundancy-based approaches, the multiple sensors can still be subject to the effects of both the environments and the attack. To the left of FIG. 8 shows the transduction shield (TS) circuits share the same vulnerabilities with the sensor but will not be sensitive to the legitimate signal. By eliminating the uncertainty, the corrupted signals can be detected or even corrected.

Figure 9:
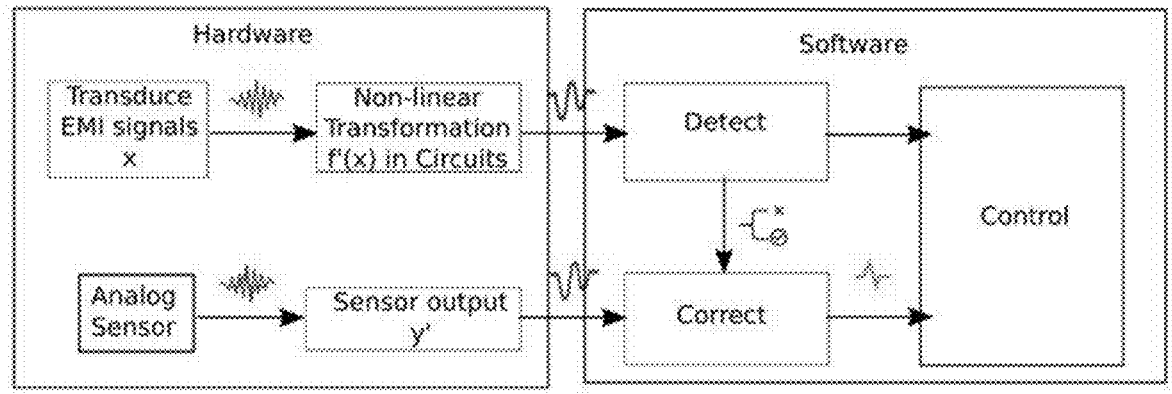
FIG. 9 shows main components of the transduction shield (TS) module to secure glucose sensors and pressure sensors, which includes software and hardware parts.

FIG. 9 shows main components of the TS module to secure glucose sensors and pressure sensors, which includes software and hardware parts.

Figure 11:
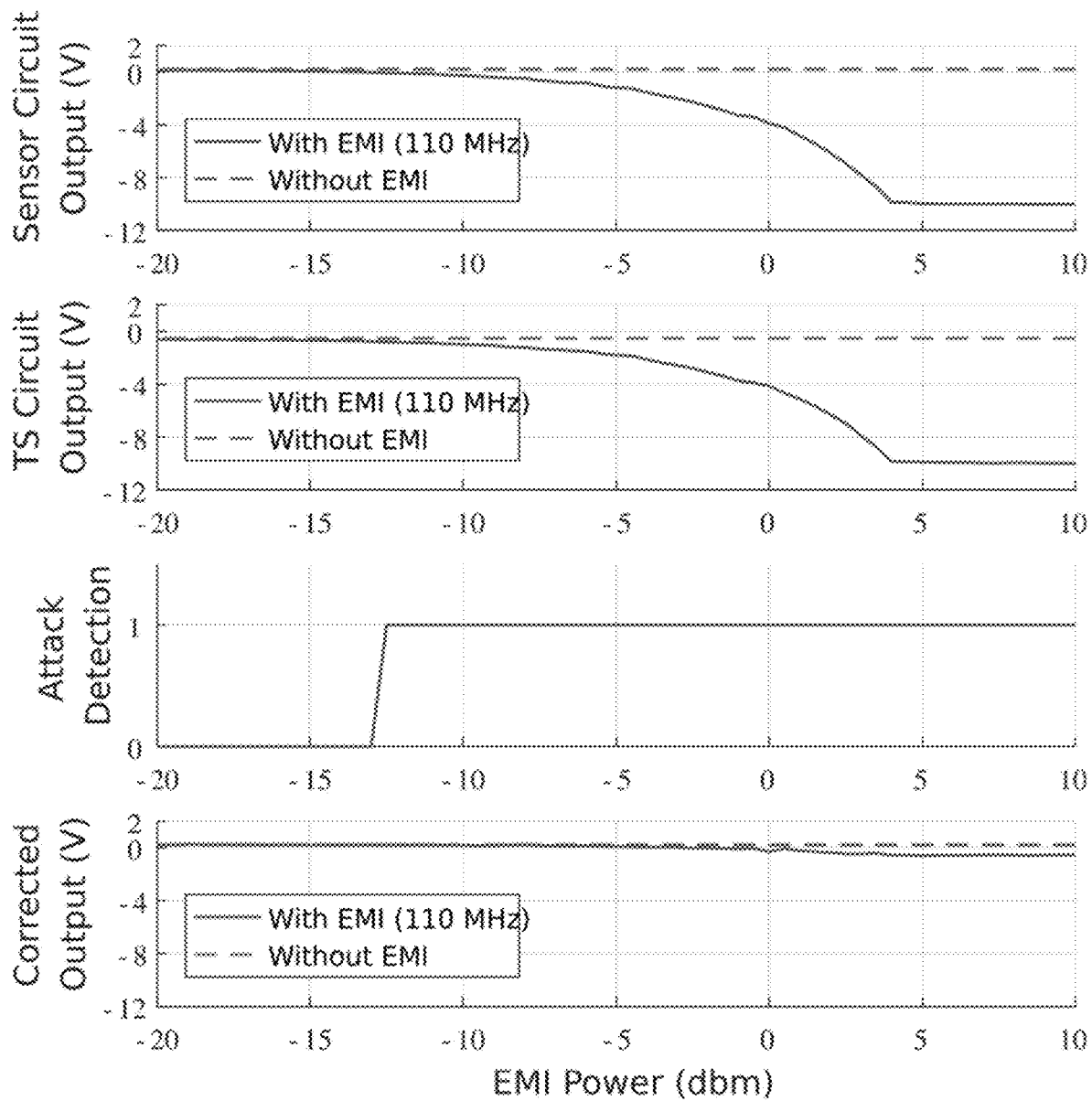
FIG. 11 shows the experiment results tested on a pressure sensor using an amplitude sweeping evaluation method.

FIG. 11 shows the experiment results tested on a pressure sensor using an amplitude sweeping evaluation method. The first two sub-figures show the output of two circuits. The third sub-figure shows the detection results and the 4th sub-figure shows the corrected data.

Figure 12:
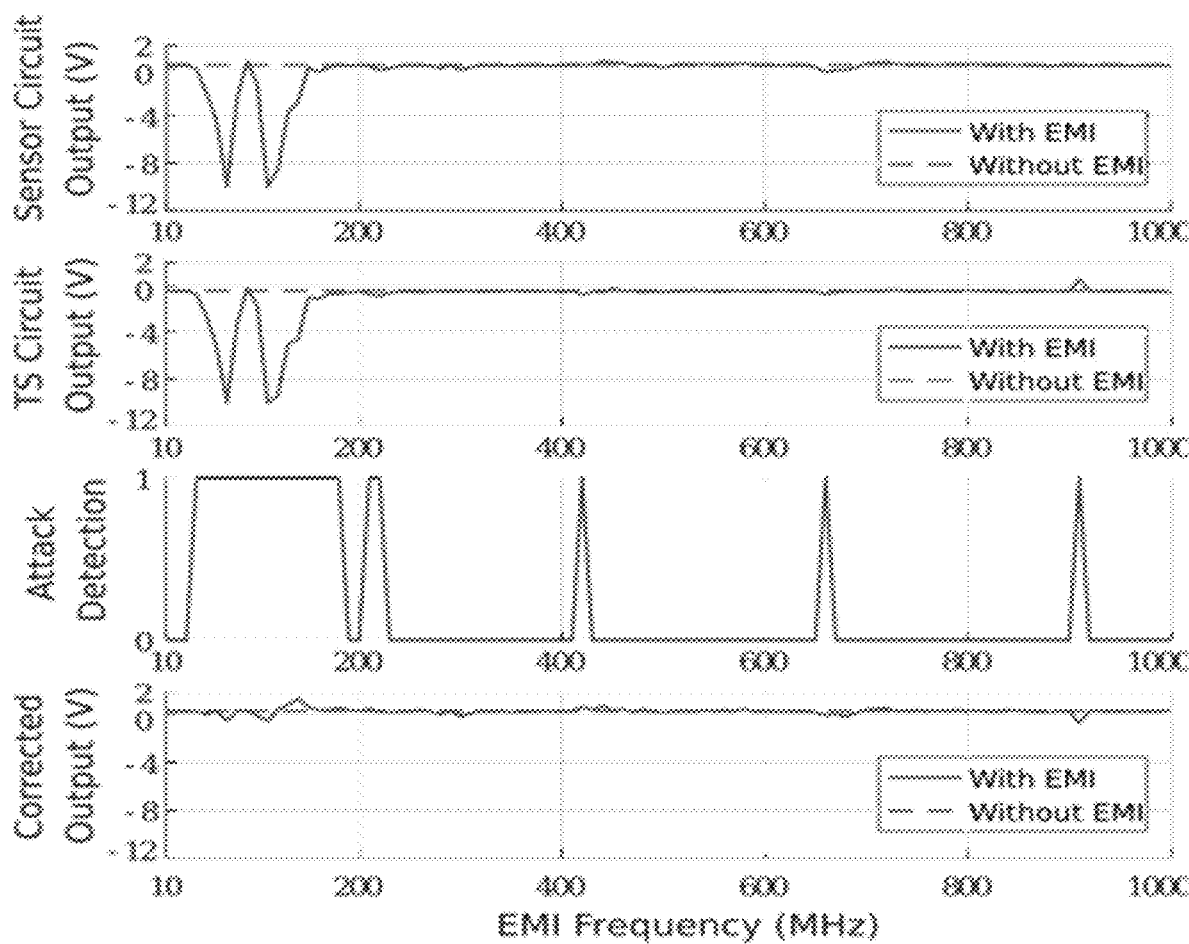
FIG. 12 shows the experiment results tested on a pressure sensor using a frequency sweeping evaluation method.

FIG. 12 shows the experiment results tested on a pressure sensor using a frequency sweeping evaluation method. The first two sub-figures show the output of two circuits. The third sub-figure shows the detection results and the 4th sub-figure shows the corrected data.

In an embodiment of the inventive method and system, the TS circuits share the vulnerabilities as the sensor to be protected. However, the TS circuits are only sensitive to EMI signals and are insensitive to the legitimate environmental signal. Due to the similarity of the circuits, the malicious signals will be transformed in the TS circuits in a similar way as the signals in the sensor circuit. In this way, the output of the TS circuits can be used to detect the attack and correct the corrupted sensor output.

The inventive method is evaluated on both pressure sensors and other sensors such as microphones. Shown herein is that the attack detection accuracy is very high.

In pressure sensors, it is shown that an error reduction rate at a minimum of 90% can be achieved. On microphones, the signal to noise ratio can be increased by 90% in white noise injection via EMI. When a malicious command is injected to dominate the original signal, the malicious signal would also be mitigated to a lower level. This will allow the software of the system to limit the induced error in a range. In this way, the system could still function.

The experimental results show that the proposed method not only detects the attack but also can correct corrupted sensor values to help maintain the proper functioning of sensor-based systems in the presence of attacks.

The goal of the countermeasure is to enable more trustworthy sensing with minimum complexity and costs. For the software layer, this is very valuable since the method reports the attack and also can provide information to limit the induced error in a range so that the system could continue to function when necessary. The method can also be used along with other methods. For instance, methods based on sensor fusion or physics models can be more accurate if the error of the sensor under EMI attacks can be limited to a certain range, which reduces the uncertainty of variables in models.

Example 2

In this example, the OhioT1DM dataset to train and test the model. This dataset includes eight weeks of data for each of six type-1 diabetes patients. The number of male and female patients was two and four, respectively. For data collection, Medtronic 530G insulin pumps and Medtronic Enlite CGM sensors were used throughout the data collection period. Each of the patients reported daily events data via a smartphone app and a fitness band. The dataset includes CGM blood glucose level every 5 minutes—288 samples per day, blood glucose levels with fingerstick (self-monitoring), insulin doses, in the form of bolus and basal, self-reported meal time with estimated carbohydrate intake, exercise time, sleep, work, stress, and illness. The data set also includes 5-minute aggregations of step count, heart rate, galvanic skin response (GSR), skin, and air temperature.

In this example, each of these attributes is analyzed to determine the optimal attribute set for the BG prediction model. Table 2 shows the number of training and test examples for each patient.

TABLE 2

Gender, number of training and test examples per patient

| Patient ID | Gender | Training Examples | Test Examples |
|---|---|---|---|
| # 559 | female | 10796 | 2514 |
| # 563 | male | 12124 | 2570 |
| # 570 | male | 10982 | 2745 |
| # 575 | female | 11866 | 2590 |
| # 588 | female | 12640 | 2791 |
| # 591 | female | 10847 | 2760 |

Initially, the accuracy of the model is determined with only the single feature—BG values. This assumes it as base accuracy. Each of the attributes is trialed only with CGM values separately and compare the accuracy with base accuracy. If the new accuracy gets better than the base accuracy, that attribute is considered as prospective. Otherwise, it is excluded.

CGM values, carbohydrate intake from the meal, insulin dose as a bolus and 5-minutes aggregation of step count from the fitness band, have a positive effect on the accuracy of the model. Thus, in one or more embodiments, this physiological signals are used in the inventive method and system.

CGM values, meal info, insulin dose, and step count info, are used as the feature set. These four features constitute the 4-channel inputs for the proposed model.

The fact that blood sugar starts to rise after 15 minutes of having the meal and reaches its peak after 1 hour. This phase is the Increasing Phase. Then the carbohydrate level in blood starts to decrease. That is the Decreasing Phase. At any time-index $t_s$, calculate the amount of carbohydrate that is effective at that moment in the blood after having a meal. The calculated amount of carbohydrates is treated as the input for the time-index $t_s$ to the model. Every time the subject encounters a meal, track and update the time-index $t_{meal}$ and the amount of carbohydrate $C_{meal}$ from the meal. Ignore the first 15 minutes (3 samples of data-point with 5 minutes of an interval) right after having a meal since it takes 15 minutes to have the effect of the meal on the blood glucose level. Thus, the equation for the effective carbohydrates $C_{eff}$ in blood for any time-index $t_s$ within the first 60 minutes of time interval after having the meal, is as follows:

$$C_{eff}(t_s) = \{(t_s - t_{meal})\beta_{inc}\} C_{meal} \quad (1)$$

Here $\beta_{inc}$ is carbs increasing factor. Use $\beta_{inc} = 0.111$, which implies that the carbohydrate level in the blood reaches its maximum (100% of the amount of carbohydrate taken from the meal) by increasing with the rate of 11.1% for every increment of time-index (5 minutes interval). Note that, $t_{meal} \geq t_s$. At the 60th minute after having the meal, $C_{eff}$ attains the maximum value by increasing with a rate of 11.1% per time-index. At that moment, the value of $(t_s - t_{meal})\beta_{inc}$ has been approximately less than or equal to 1.00.

Do not consider the first 15 minutes (3 time-indexes) right after having the meal in the above equation; instead, consider nine time-indexes out of twelve time-indexes within 60-minutes interval so that the value of $C_{eff}$ doesn't exceed 100% of $C_{meal}$. When $C_{eff}$ reaches its maximum, then the decreasing phase begins. Calculate the amount of carbohydrate effective or appeared in the blood as glucose at any particular time-index $t_s$ within the decreasing phase is as follows.

$$C_{eff}(t_s) = C_{meal}\{1 - (t_s - t_{meal})\beta_{dec}\} \quad (2)$$

Here, $\beta_{dec}$ is the carbs decreasing factor. Set the value of $\beta_{dec}$ as 0.028 according to the assumption that the duration of the decreasing phase is around 3 hours. This means that after 3 hours (the number of time-index is 36), $C_{eff}$ would be approximately near to 0.00. Update $C_{eff}$ in every steps where, $C_{eff}$=max(0, $C_{eff}$). Thus, ignore any negative values for $C_{eff}$.

Use crafted insulin information as one of the four inputs to the proposed RNN model. Consider only bolus information for further crafting.

Basal insulin has no considerable effect on blood glucose prediction accuracy. There are two pathways of insulin absorption, slow and fast. Approximately 67% of delivered insulin passed through the slow channel with an average absorption rate of 0.011 min$^{-1}$, whereas 33% of insulin passed through the fast one with an absorption rate of 0.021 min$^{-1}$. Therefore, use the weighted average of these two absorption rates, which is 0.014 min$^{-1}$. For every five minutes interval, it is denoted with $R_{insulin}$=5*0.014. Calculate the effective insulin on the body $I_{eff}$ at any particular time-index $t_s$ with the equation as follows:

$$I_{eff}(t_s)=I_{bolus}-(t_s-t_{bolus})R_{insulin} \quad (3)$$

Here, $I_{bolus}$ is the amount of insulin delivered in the form of bolus to the patient, and $t_{bolus}$ is the time-index when the most recent insulin delivered to the patient. Update $I_{eff}$ in every steps, where $I_{eff}$=max(0, $I_{eff}$). This calculated effective insulin in the body $I_{eff}$ is used as one of the inputs for the RNN model. In the above equation, do not consider insulin absorption delay.

Compute a weighted average of the number of steps taken by the patient at time $t_s$. To calculate $S_{avg}$, consider the previous 50 minutes (10 readings with 5 minutes of the interval) where the steps count for most recent time-index has a more significant weight. Note that the weight decreases gradually with time-index.

$$S_{avg}(t_s) = \frac{1}{n}\sum_{i=0}^{n-1}(n-i)\times steps(t_s-i) \quad (4)$$

In the above equation, n=10 as only the previous 50 minutes or 10 data points are considered. The computed $S_{avg}$ is treated as one of the inputs.

Figure 13:
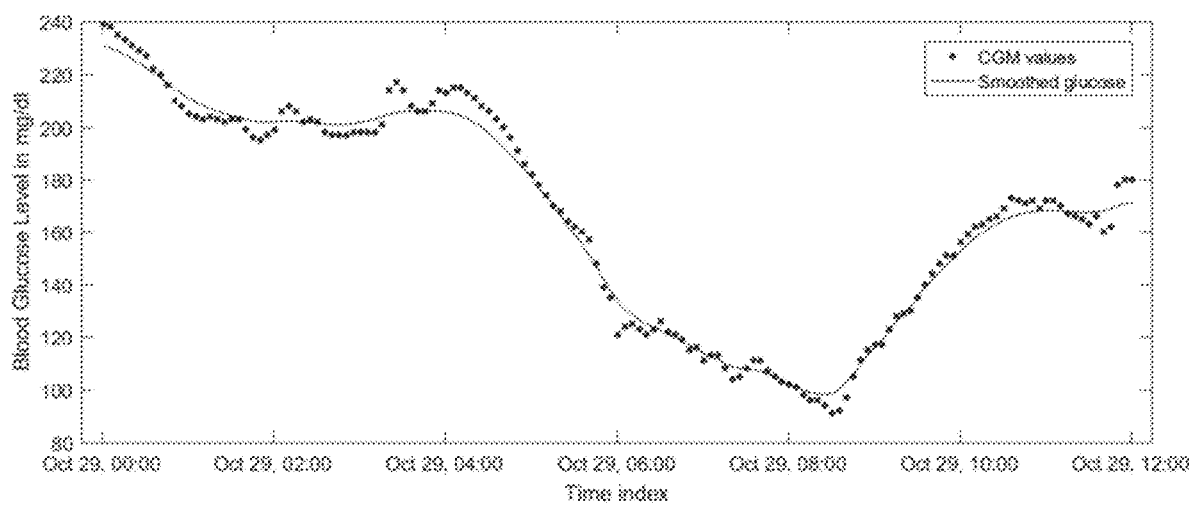
FIG. 13 shows Kalman smoothed CGM values vs raw CGM readings for 12 hours' time window from the patient #563.

FIG. 13 shows Kalman smoothed CGM values vs raw CGM readings for 12 hours' time window from the patient #563. Here dots are raw CGM readings, where the blue line is the smoothed CGM values.

Either unprocessed or Kalman smoothed CGM readings are considered as an input channel out of the four inputs.

The KS method outputs an interpolated time series of glucose estimates with mean and variance. It can automatically correct errors in the CGM readings where the estimated variance can be utilized for determining at which times the data are reliable.

KS is used as a pre-processing technique for sensor fault correction in the CGM reading. Use a modified implementation of KS for the OhioT1DM dataset. The Kalman filter is a technique of estimating the current state of a dynamical system from the previous observations. In Kalman filtering, records of data are used for the calculation of the estimates. Thus, the Kalman filter is appropriate for real-time data processing. It is a forward algorithm where each step is computed analytically. The model and observation can be written as:

$$x_{k+1}=\phi_k x_k + B_k u_k + W_k \quad (5)$$

$$y_k=H_k x_k + v_k \quad (6)$$

Here, x, u, and y are the system internal state, input to the system, and measured output respectively. Whereas v is the process noise, and w is the measurement noise. These noise processes are assumed to be zero-mean Gaussian. $\phi$ is the transition matrix, and H is the measurement matrix.

In the phase of time update, the Kalman filter computes the priori estimates, a state estimate x and state covariance matrix P.

$$x_k=\phi_{k-1}\hat{x}_{k-1}+B_{k-1}u_{k-1} \quad (7)$$

$$P_k=\phi_{k-1}\hat{P}_{k-1}\phi_{k-1}^T+Q_{k-1} \quad (8)$$

Then the phase measure update is performed, where the posteriori estimate $\hat{x}$ and $\hat{P}$ are calculated. The equations are as follows:

$$K_k=P_k H_k^T(H_k P_k H_k^T+R_k)^{-1} \quad (9)$$

$$\hat{x}_k=K_k(y_k-H_k x_k) \quad (10)$$

$$\hat{P}_k=(I-K_k H_k)P_k \quad (11)$$

Kalman smoothing can be applied to get better estimates than Kalman filtering. However, it is required to have the whole dataset available at the time of performing Kalman smoothing.

The Rauch-Tung-Striebel (RTS) algorithm uses previous as well as the following data at the time k to generate the estimate. In RTS, there is one forward pass through the available data applying the Kalman filter to generate the priori, posteriori, and covariance matrices. These generated estimates and covariance are then treated as input to a subsequent backward pass. In this phase, RTS calculates the smoothed estimate $\hat{x}_k^s$ and $\hat{P}_k^s$.

$$C_k=\hat{P}_k\phi_k P_{k+1}^{-1}-1 \text{ mm} \quad (12)$$

$$\hat{x}_k^s=x_k+C_k(\hat{x}_{k+1}^s-x_{k+1})-1 \text{ mm} \quad (13)$$

$$\hat{P}_k^s=\hat{P}_k+C_k(\hat{P}_{k+1}^s-P_{k+1})C_k^T-1 \text{ mm} \quad (14)$$

Apply Kalman smoothing on CGM readings from the OhioT1DM dataset to get smoothed CGM values. Original CGM readings (represented by dots) and smoothed CGM values (represented by the blue line) are shown. It is noticeable that, after applying Kalman smoothing, there are less abrupt changes or fluctuations in smoothed CGM values.

The inventive model uses a neural network to learn the prediction. A recurrent neural network (RNN) is a feedforward neural network that can model sequential data. It uses weight sharing between each element in the sequence over time. There are diverse variants of RNN. In the basic RNN variant termed as Vanilla RNN, the transition function is a linear transformation of the hidden state vector h and the input vector x, followed by an activation function for non-linearity.

$$h_t=\tan h(W[h_{t-1},x_t]+b) \quad (15)$$

Where W is weight matrix, b is a bias vector, and tan h is the activation function. Classical RNN has the form of a chain of repeating modules of neural networks with straightforward architecture. Theoretically, RNN can learn long term dependency. However, practically it suffers from vanishing gradient problem and exploding gradient problem as a result of long term dependency. This dependency makes RNN less useful and more challenging to train.

Prior art has proposed Long short-term memory (LSTM) for addressing this issue. The LSTM network mitigates this long-term dependency problem to some extent by utilizing the concept of memory, the gate structure, and constant error carousel. In the case of the study, LSTM is more suitable to model blood glucose levels as there are dependencies upon immediate previous entries in sequential diabetes patient data. Consequently, the LSTM based RNN model over the other model architectures is preferred to make the BG prediction more rigorous.

Figure 4:
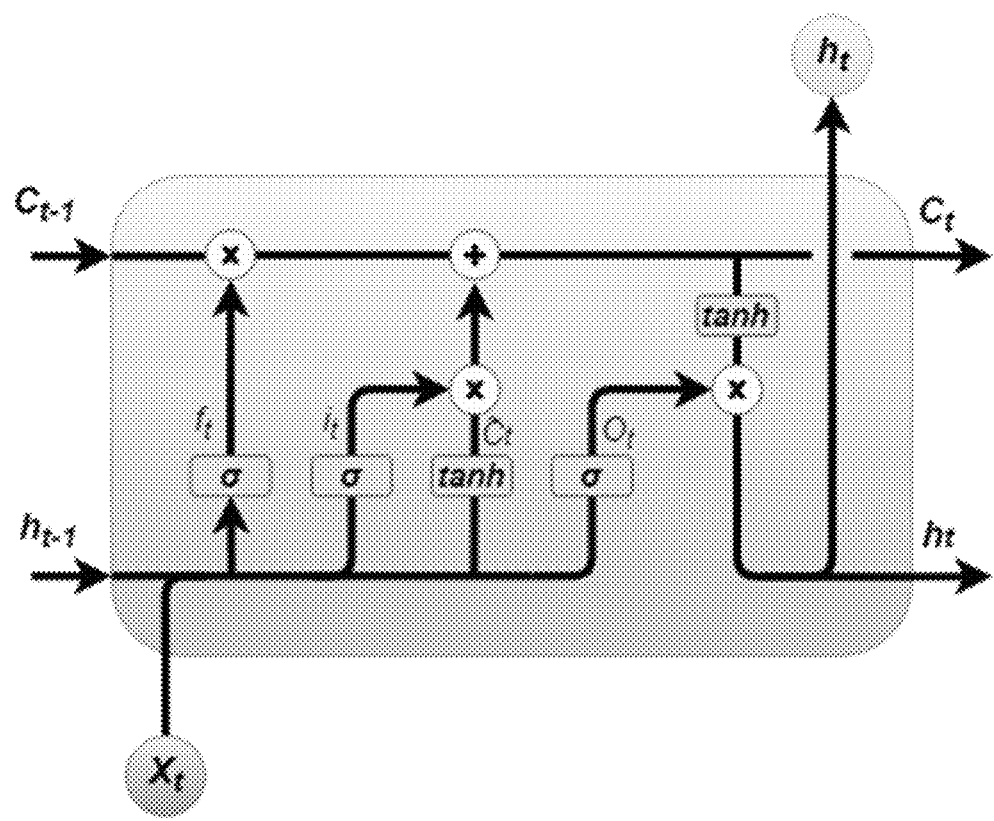
FIG. 4 shows the LSTM Based Deep Recurrent Neural Network.

FIG. 4 shows the Structure of an LSTM cell.

This inventive method and system builds an LSTM network containing 128 element hidden vector. Each cell at step t includes a forget gate $f_t$, an input gate $i_t$, a control gate $\tilde{C}_t$, an output gate $o_t$, and an internal cell memory $C_t$.

The first gate is the forget gate $f_t$ that determines which information can be carried to the cell from the output of the previous LSTM cell. It is a single layer neural network, that can be represented as:

$$f_t = \sigma(W_f[h_{t-1}, x_t] + b_f) \quad (16)$$

The input gate $i_t$ controls how much the new memory should influence the old memory. It can be written as:

$$i_t = \sigma(W_i[h_{t-1}, x_t] + b_i) \quad (17)$$

The control gate $\tilde{C}_t$ generates new memory and updates cell state from $C_{t-1}$ and $\tilde{C}_t$. Here $\odot$ represents element-wise multiplication.

$$\tilde{C}_t = \tan h(W_C[h_{t-1}, x_t] + b_C) \quad (18)$$

$$C_t = f_t \odot C_{t-1} + i_t \odot \tilde{C}_t \quad (19)$$

The output gate is responsible for modulating the output to obtain $h_{t-1}$. It can be expressed with the equation below:

$$o_t = \sigma(W_o[h_{t-1}, x_t] + b_o) \quad (20)$$

$$h_t = \tan h(C_t) \odot o_t \quad (21)$$

In the above equations, $W_s$ is the corresponding weight matrix, $\sigma$, and tan h are sigmoid and hyperbolic tangent activation function, respectively.

Add a dropout layer after the LSTM layer. Dropout is intended to reduce overfitting and improve the generalization of the model. The last layer of the LSTM outputs a vector $h_t$, which is fed as the input of a fully connected multi-layer network. This network consists of three layers, including two hidden layers and one output layer. These dense layers contain 512 neurons, 128 neurons, and a single neuron, respectively, with an activation function each.

Use the rectified linear unit (ReLU) activation function for the first two dense layers and the exponential activation function for the output layer. The final output of the network can be represented as follows:

$$[\mu, \sigma^2] = \text{activation}(W_f h_t + b_f) \quad (22)$$

Here $\mu$ is the mean, and $\sigma^2$ is the variance. Evaluate the confidence of the model with these values. The input of the model is a multi-dimensional sequence of preprocessed BG level from CGM reading, carbohydrates amount from the meal, carbohydrates amount from the bolus, and step count related data. The output of the model is a prediction regarding BG level within a prediction horizon. Analyze the prediction horizon of 30 and 60 minutes. The proposed model adopts the negative log-likelihood (NLL) loss function as follows:

$$L = \frac{1}{k} \sum_{i=0}^{k} -\log(f(y_i | \mu_i, \sigma_i^2)) \quad (23)$$

In the above equation, $y_i$ is the target BG value, and $\mu_i$, $\sigma_i$ are the mean and SD respectively for the output of the model for corresponding input $x_i$. The function $f$ represent the difference between target and output BG value. Use Adaptive Moment Estimation (Adam) as the optimizer.

This example also studies the correlation between BG prediction accuracy and depth of the model architecture. In previous prior art work, the deep recurrent neural networks provide empirical superiority over shallow networks. The shallow network cannot precisely model the information with a temporal hierarchy. However, the concept of depth in an RNN is not the same as it is in feedforward neural networks.

Figure 4A:
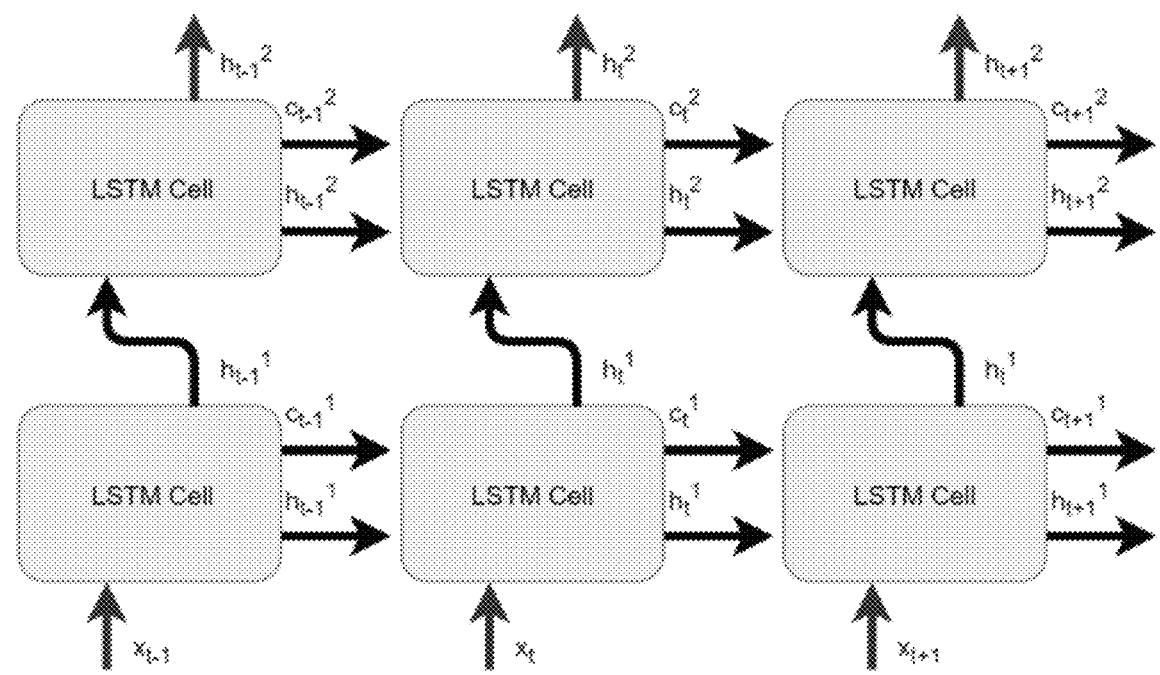
FIG. 4a shows a Two Layered Stacked LSTM network.

To make the RNN model deeper, in one or more embodiments, this inventive method and system employs the stacking technique. It consists of two LSTM layers. The first LSTM layer provides a sequence output that is fed as one input to the LSTM layer above. Both LSTM layers have the same internal architecture described earlier. FIG. 4a illustrates the architecture of two Layered Stacked LSTM.

This example also analyzes the GRU cell instead of the LSTM cell. However, in this application, the network with the LSTM cell outperforms the network with GRU cells. A comparison between the performance of these two types of RNN is discussed below.

This example shows how to tune hyperparameters and determine the optimal setup. Measure the efficacy of the proposed method to predict BG values for two different setups. In the first setup, use raw CGM readings, whereas, in the second setup, use Kalman smoothed CGM values for sensor error correction.

LSTM and GRU cells are analyzed. The dynamics of the glucoregulatory system are considered as nonlinear. Hence, learning blood glucose dynamics is a complicated task where consideration of previous data is very crucial for effective prediction mechanisms. As a consequence, skip experimenting with Vanilla RNN cells because of its long term dependency problem.

The examples demonstrates that the LSTM network achieves better prediction accuracy than a network with GRU cells. The inventive system and method is demonstrated using the six patients' training data from the OhioT1DM dataset. 30, 60, 120, and 240 minutes of data history as the input for the proposed model are provided. Those contain 6, 12, 24, and 48 training examples respectively as CGM readings are taken with every five minutes of interval. Investigate the effect of the number of LSTM state hidden units and fully connected layers in the network. Different combinations of LSTM state size-of 64, 128, and 248 with two fully connected layers are tested. The network model with 128 LSTM states with two fully connected layers outperforms other configurations. A learning rate of $10^{-3}$ was used for training with a maximum number of 6000 epochs. However, an early-stopping patience threshold of 128 epochs is employed for better convergence.

Use the T1DM dataset for training, validation, and testing purposes. This dataset contains 12 files for six data contributors. For each person, there are two files for training and testing data, respectively. Split the data in the training file into the training and validation dataset. The entire dataset in the testing file is used for testing purposes for each subject. Partition the training data file such that 80% of the data is used for training, and the rest of the data is used for validation. The purpose of the validation data is to provide an evaluation of the model after hyperparameter tuning.

In the training phase, the prediction from the model is used to determine the subsequent prediction curve at each epoch. It is possible to evaluate the model at a certain point in time if there are at least 24 prior data points are available (prior data points for 2 hours or 120 minutes). This threshold is to assure that there are enough data points available for the model to make a feasible prediction. For the training process, set the batch size to 128. However, try with larger batch sizes than 128 and found that it makes the prediction accuracy worse in terms of RMSE. Finally, train the two instances of the model separately with raw CGM data, and Kalman smoothed CGM data, respectively, along with other features including carbohydrates from the meal, bolus insulin, and cumulative step counts in a fixed time interval. Consider the previous 50 minutes of history for calculating the cumulative step numbers.

The performance of the model is compared based on the accuracy over the 30 and 60 minutes prediction horizon. The hyperparameters of the model are tuned extensively for optimal results.

Use Kalman smoothing for processing the CGM readings. Compare the deviation of raw CGM readings and preprocessed CGM values from the ground truth reference value. In the analysis, assume the BG level measured by fingerstick as ground-truth. The glucose readings from the sensor sampling in interstitial fluid are substantially different from blood glucose values measured at the same time. As a result, CGM manufacturers suggested that patients should use capillary blood glucose measurements before any treatment decisions. Moreover, the self-measurement of blood glucose (SMBG), has been used as a reference for different CGM systems accuracy comparison. Fingerstick testing is one of the most convenient SMBG methods. These are the principal reasons behind the assumption of choosing the fingerstick reading as the ground truth for comparison between raw CGM value and preprocessed CGM values. Use Mean Absolute Error (MAE) to calculate the difference between CGM values (raw CGM, preprocessed CGM) and fingerstick reference BG values at a particular time.

$$MAE = 1/N \sum_{i=1}^{N} |y_i - x_i| \quad (24)$$

Here, y denotes the CGM values (either raw CGM values or smoothed CGM values), and x denotes the fingerstick reference BG values.

Preprocessed CGM values are much closer to fingerstick BG reading than raw CGM values. Table 3 illustrates the accuracy comparison, in terms of MAE, between raw CGM and Kalman smoothed CGM values with respect to fingerstick BG readings. Table 3 shows that both of the CGM readings (measured from interstitial fluid) and pre-processed CGM values differ from finger stick reading (measure from blood glucose). However, most importantly, processed CGM values have a lower error than raw CGM values. Thus, the model trained with Kalman smoothed CGM values along with other features, is more effective in forecasting the BG level.

TABLE 3

Comparison of the accuracy (MAE) of raw CGM values and Kalman Smoothed CGM values with respect to fingerstick BG readings

| Patient ID | # of Fingerstick | Raw CGM | Smoothed CGM |
|---|---|---|---|
| # 559 | 53 | 21.7 | 19.8 |
| # 563 | 196 | 16.0 | 14.7 |
| # 570 | 99 | 10.3 | 9.5 |
| # 575 | 117 | 9.7 | 10.5 |
| # 588 | 391 | 20.8 | 18.4 |

TABLE 3-continued

Comparison of the accuracy (MAE) of raw CGM values and Kalman Smoothed CGM values with respect to fingerstick BG readings

| Patient ID | # of Fingerstick | Raw CGM | Smoothed CGM |
|---|---|---|---|
| # 591 | 197 | 18.7 | 17.4 |
| Mean MAE | N/A | 16.2 | 15.1 |

However, the performance of a model can be evaluated with different criteria. Among those, the root-mean-square error (RMSE) between the reference CGM values and predicted BG level, is one of the most widely adopted methods to assess the BG prediction accuracy. Thus, the performance of the inventive model in terms of RMSE was analyzed.

$$RMSE = \sqrt{\frac{1}{N} \sum_{i=0}^{N} (\hat{y}(i|i - PH)^2 - y(i))^2} \quad (25)$$

Where $\hat{y}(i|i-PH)$ denotes the model's prediction results provided the previous data and y denotes the reference CGM reading, N is the number of data points.

The BG forecasting accuracy for the proposed stacked RNN model for the OhioT1DM dataset, where CGM readings are raw/unprocessed was analyzed. Investigate the effect of the depth of LSTM layers of the network on the prediction accuracy of the model. Consider the prediction horizon of 30 and 60 minutes. The experimental results for models with single LSTM layers and stacked LSTM layers are summarized in table 3. Results from the table demonstrate that the RNN model with stacked LSTM layered architecture performs better than RNN with a single LSTM layer for all of the cases.

Table 4 below shows the prediction comparison of proposed models over 30 and 60 minutes of the prediction horizon. Here, the models are trained with the raw CGM readings along with the other three features mentioned before. The first one is the RNN model having a single LSTM layer, whereas the second one is stacked LSTM based deep RNN model.

TABLE 4

| | PH = 30 min | | PH = 60 min | |
|---|---|---|---|---|
| 3* Patient ID | Single LSTM | Stacked LSTM | Single LSTM | Stacked LSTM |
| # 559 | 18.03 | 17.85 | 31.89 | 31.55 |
| # 563 | 19.20 | 18.65 | 31.01 | 30.42 |
| # 570 | 16.63 | 15.94 | 26.28 | 25.74 |
| # 575 | 21.12 | 20.93 | 32.90 | 31.97 |
| # 588 | 18.07 | 17.71 | 31.11 | 30.45 |
| # 591 | 20.71 | 20.35 | 32.06 | 31.80 |
| Mean (RMSE) | 18.96 | 18.57 | 30.88 | 30.32 |

Figure 14:
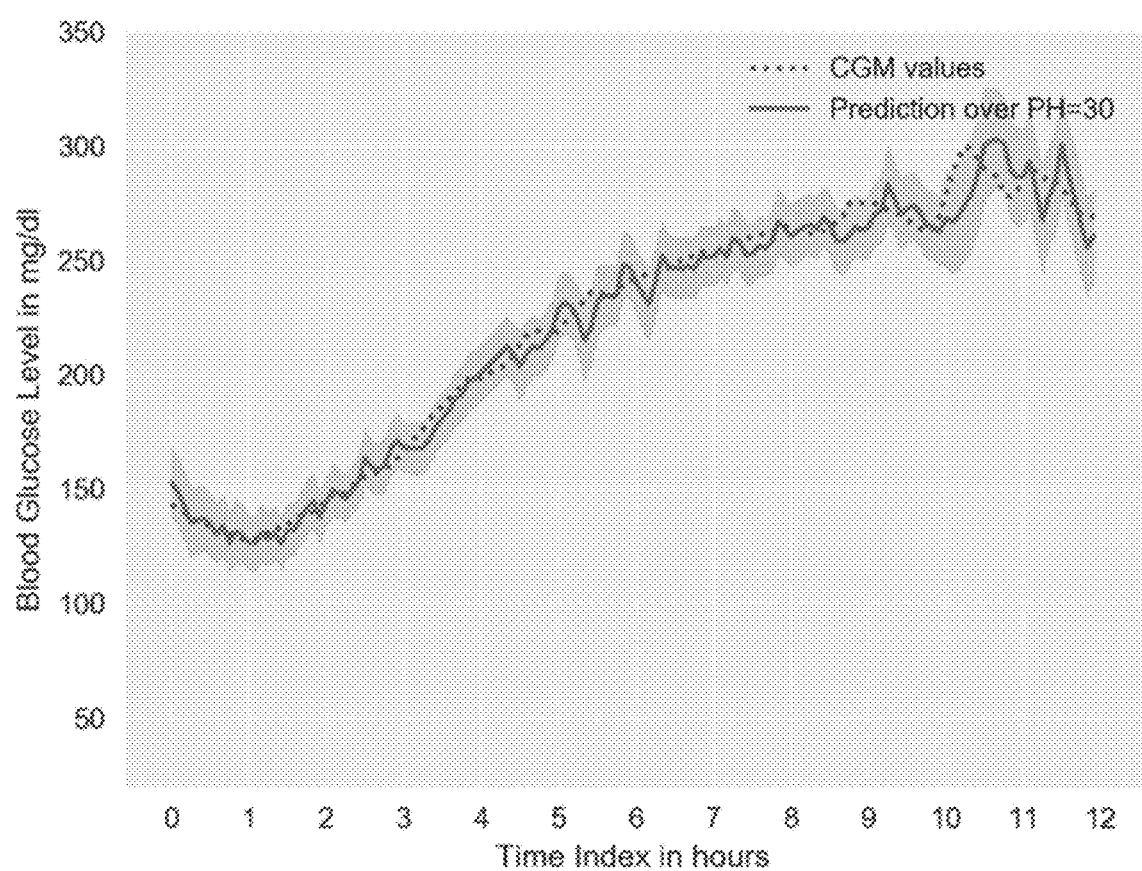
FIG. 14 shows a model of 12-hours of prediction results over PH+30 for patient #570.
Figure 15:
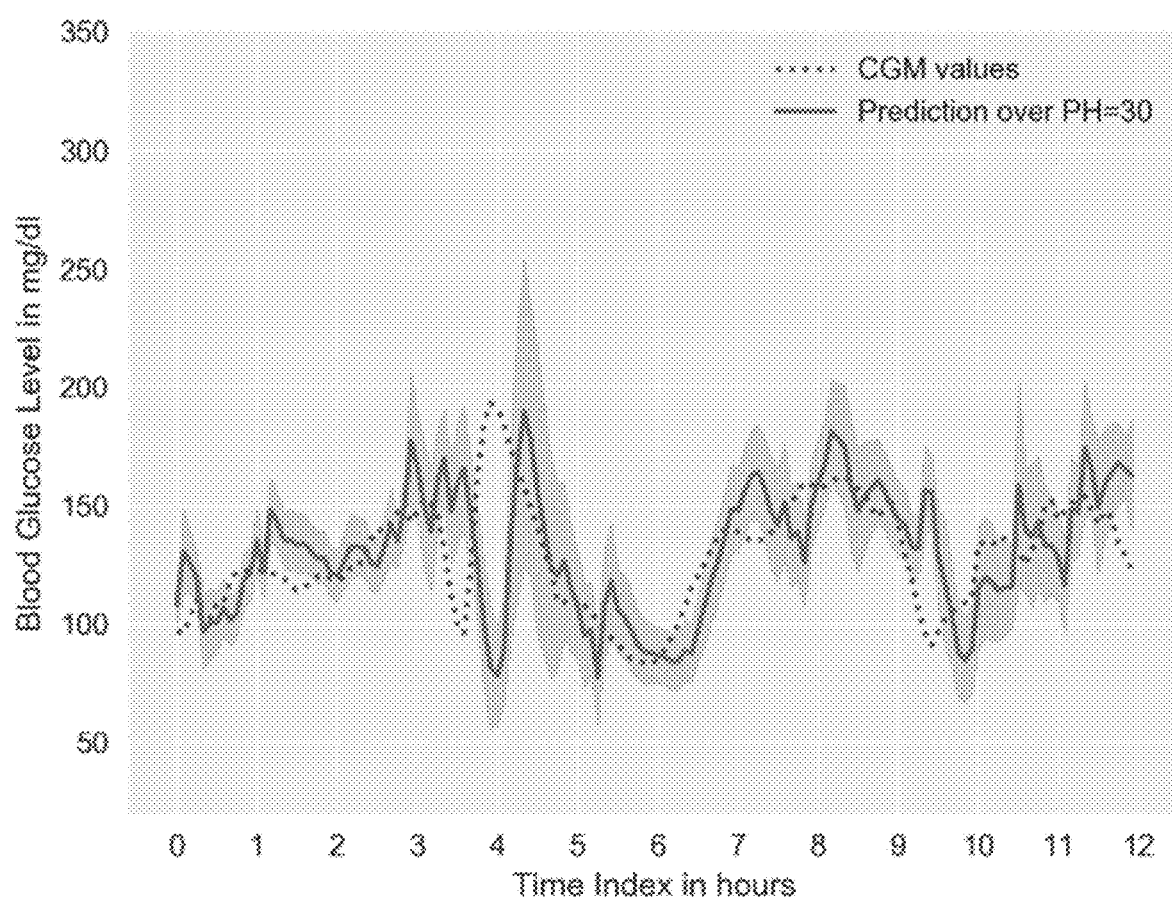
FIG. 15 shows a model of 12-hours of prediction results over PH+30 for patient #575.

The proposed model's (Stacked LSTM) predictive results for patient #570 and #575 over PH=30 minutes are illustrated in FIGS. 14 and 15. The proposed model provides the lowest and the highest RMSE result for patient #570 and patient #575 respectively.

FIG. 14 shows a model of 12-hours of prediction results over PH+30 for patient #570. FIG. 15 shows a model of 12-hours of prediction results over PH+30 for patient #575.

Here dots are CGM readings (unprocessed); those are ground truths. Where the blue line is the prediction curve, and the light blue region is the standard deviation.

The example also analyzes single GRU cell-based RNN for BG level prediction. However, both of the models with single and stacked LSTM cells provide better RMSE than the model with the GRU cell. The mean RMSE for the six patients' BG prediction are 20.07 and 31.12 for the PH=30 and 60 minutes respectively.

The proposed model's predictive accuracy with stacked LSTM layers was evaluated for the preprocessed testing dataset with Kalman smoothing technique. Only CGM values are preprocessed, and the rest of the features remain the same. Then estimate the RMSE of the model's prediction individually with preprocessed CGM values and raw CGM values, respectively, from the testing dataset as the goal is to lower the difference between the predicted CGM values and the real fingerstick blood glucose readings.

Table 5 presents the forecasting accuracy (RMSE) of the model trained with the preprocessed (CGM values) dataset using the Kalman smoothing technique and original (raw CGM values) dataset.

The prediction result is for the dataset with raw CGM readings, and Kalman smoothed CGM values, respectively, over 30 minutes and 60 minutes of the prediction horizon.

TABLE 5

| Patient ID | PH = 30 min | | PH = 60 min | |
|---|---|---|---|---|
| | Smoothed CGM | Raw CGM | Smoothed CGM | Raw CGM |
| # 559 | 4.73 | 17.85 | 16.17 | 31.55 |
| # 563 | 5.74 | 18.65 | 16.31 | 30.42 |
| # 570 | 4.81 | 15.94 | 14.22 | 25.74 |
| # 575 | 8.45 | 20.93 | 22.12 | 31.97 |
| # 588 | 5.10 | 17.71 | 15.73 | 30.45 |
| # 591 | 6.53 | 20.35 | 18.88 | 31.80 |
| Mean (RMSE) | 5.89 | 18.57 | 17.24 | 30.32 |

Table 5 demonstrates that preprocessing the CGM reading with Kalman smoothing, improves the prediction accuracy to a substantial extent.

It is evident that, with a wider prediction horizon, the forecasting model becomes more complicated. However, deep approaches with stacked LSTM layers provide advantages over the shallow model with a single LSTM layer in forecasting BG level, particularly for a higher prediction horizon. As a result, the deeper model is chosen for a final example.

From Table 5, prediction RMSE for each patient ranges from 15.94 to 20.94 and 4.73 to 8.54 for the model trained with raw CGM readings and processed CGM readings, respectively. The predictions for patients #575 and #591 are comparatively more inaccurate than other patients, whereas this example achieved better RMSE for patient #570 and #588. There might be several reasons for the RMSE difference. The first reason is that #575 and #591 have a larger number of missing data. On the other hand, #570 has the least missing data among all of the patients' test dataset. Another reason is that the fluctuation of CGM readings in the test dataset. It is noticeable that in the test dataset, #575 and #591 have substantially more fluctuation than #570 and #588. More specifically, the last portion of #575 and the first portion of #591 have more abrupt swings. 12-hours period BG level of #570 contains less fluctuation than #575. It is noteworthy that the prediction error is highest around the spikes and turning regions of the CGM trajectory. Furthermore, there is a marginal time delay in the prediction curve. This delay is responsible for the prediction error.

Such abrupt fluctuations in training and testing dataset make it difficult for the model to learn and predict the BG level accurately. One of the possible reasons behind such fluctuation is the complicated dynamic of the glucoregulatory system. Another possible reason is the sensor fault of the CGM system. Mitigate such undesirable errors by applying the Kalman smoothing technique on the dataset that makes CGM values less likely to have abrupt fluctuations. Subsequently, it boosts the learning capability of the model resulting in significantly better prediction accuracy.

Figure 5:
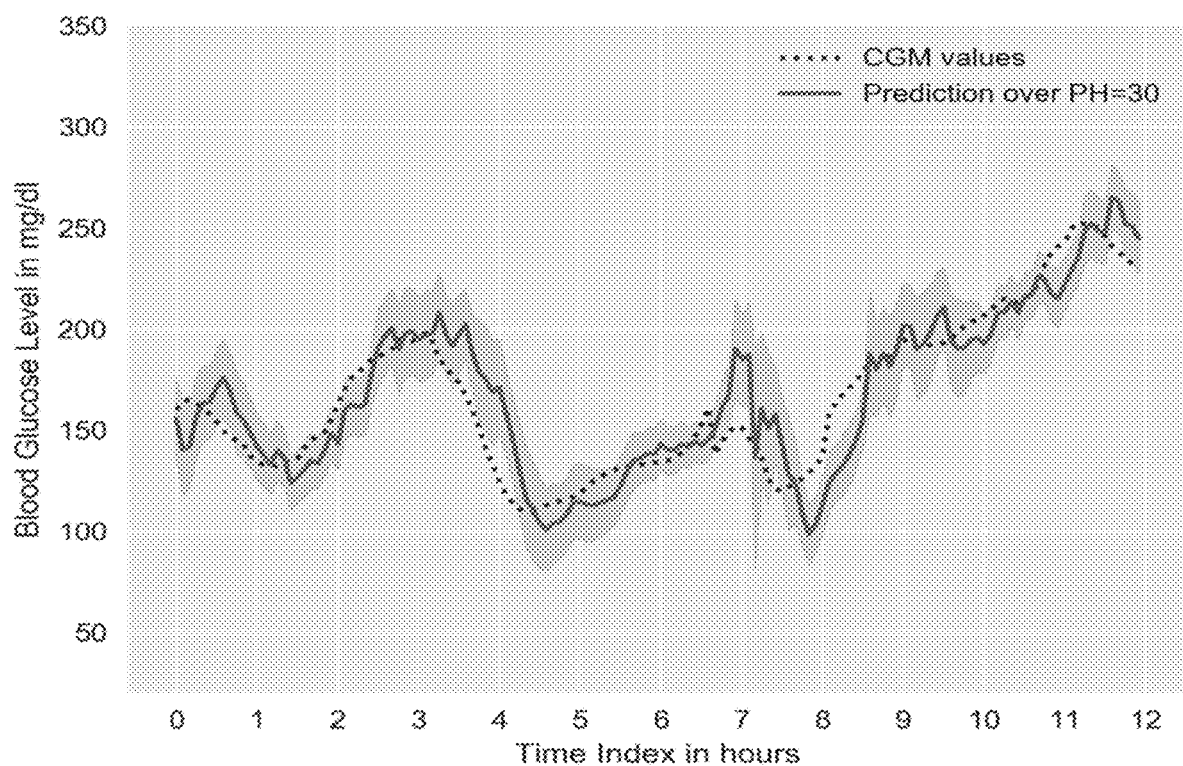
FIG. 5 shows the glucose prediction using LSTM Based Deep Recurrent Neural Network without Kalman filter.
Figure 6:
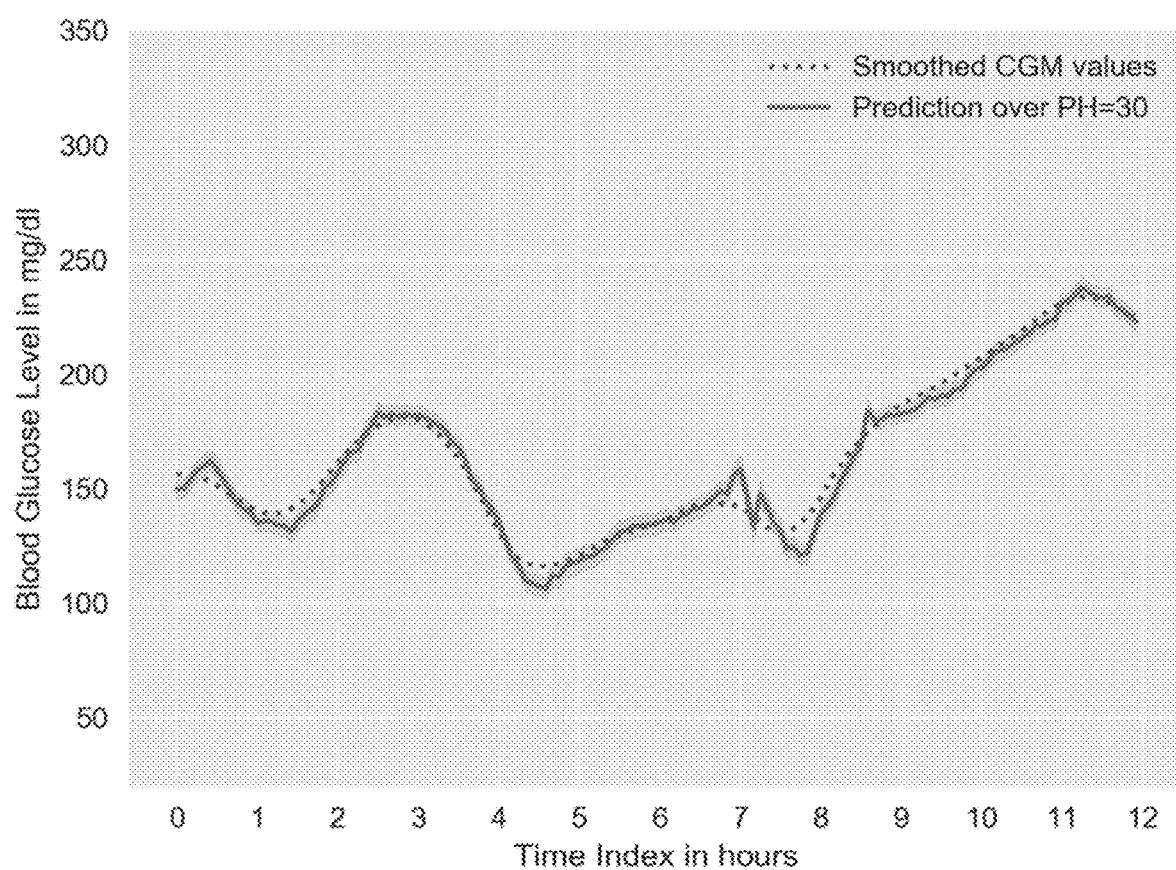
FIG. 6 shows the glucose prediction using LSTM Based Deep Recurrent Neural Network with Kalman filter.

FIGS. 14 and 15 illustrates how error correction of CGM reading, enhances the precision of the prediction curve for a particular 12-hours time window for patient #563. Here use patient #563 as the dataset for this patient has average fluctuation. The SD (shaded region) is remarkably less for the prediction made with the model trained with processed data. Hence, the model trained with the error corrected dataset (FIG. 6), is capable of forecasting BG with more confidence than the model trained with the unprocessed dataset (FIG. 5). Moreover, an improvement in the time delay in the inventive method and system is shown.

Table 6 shows the prediction accuracy comparison, in terms of RMSE, between the proposed model and models from related works for the OhioT1DM dataset (PH=30 minutes).

TABLE 6

| Patient ID | RMSE w/KS | RMSE w/o KS | RMSE of prior art 1 | RMSE of prior art 2 | RMSE of prior art 3 |
|---|---|---|---|---|---|
| # 559 | 4.73 | 17.85 | 18.78 | 19.50 | 22.48 |
| # 563 | 5.74 | 18.65 | 18.12 | 19.00 | 20.35 |
| # 570 | 4.81 | 15.94 | 15.46 | 16.40 | 18.26 |
| # 575 | 8.45 | 20.93 | 22.83 | 24.80 | 25.65 |
| # 588 | 5.10 | 17.71 | 17.72 | 19.30 | 21.69 |
| # 591 | 6.53 | 20.35 | 21.34 | 25.40 | 24.59 |
| Mean | 5.89 | 18.57 | 19.04 | 20.73 | 22.17 |

Provide a performance comparison of the work with related works for the OhioT1DM dataset in Table 6. For comparison, consider prior art works which use the OhioT1DM dataset for result evaluation. Table 6 demonstrates that the proposed model with KS provides the best accuracy for every patient among all other related works. Even without utilizing KS, the inventive method and system achieved the topmost accuracy for the four patients out of six.

This inventive method and system provides a more accurate blood glucose prediction. Preprocessing the CGM readings with Kalman smoothing for sensor error correction improves the robustness of the BG prediction.

In one or more embodiments, the inventive system and method uses one or more physiological information such as meal, insulin, aggregations of step count, and preprocessed CGM data.

The invention provides a novel approach for leveraging the stacked LSTM based deep RNN model to improve the BG prediction accuracy.

Preprocessing the CGM values with Kaman smoothing makes the BG prediction curve less uncertain and less fluctuating. Thus, this invention provides more reliable predictions than traditional methods. This more accurate prediction can aid diabetes patients to avoid adverse glycemic events. The inventive method and system may be used to provide insight into T1D patient's future BG level trends that might result in a more dependable diabetes management system.

For the purpose of understanding the DIABETES DETECTION SYSTEM, references are made in the text to exemplary embodiments of an DIABETES DETECTION SYSTEM, only some of which are described herein. It should be understood that no limitations on the scope of the invention are intended by describing these exemplary embodiments. One of ordinary skill in the art will readily appreciate that alternate but functionally equivalent components, materials, designs, and equipment may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

Reference throughout this specification to features, advantages, or similar language does not imply that all of the features and advantages that may be realized should be or are in any single embodiment. Rather, language referring to the features and advantages is understood to mean that a specific feature, advantage, or characteristic described in connection with an embodiment is included in at least one embodiment. Thus, discussion of the features and advantages, and similar language, throughout this specification may, but do not necessarily, refer to the same embodiment.

The invention claimed is:

1. A system for determining a false alarm in a continuous glucose monitor comprising:
   a. a patient physiological signal detector, wherein said signal detector continuously monitors a plurality of patient physiological signals selected from the group consisting of heart rate, galvanic skin response, skin tremor, and heart rate variability, and wherein said signal detector outputs said monitored patient physiological signals;
   b. a continuous glucose sensor, wherein said glucose sensor outputs measured patient glucose levels;
   c. an insulin pump operably connected to said continuous glucose sensor, wherein said insulin pump injects the patient with insulin based on said measured patient glucose levels;
   d. a receiver operably connected to said continuous glucose sensor, said patient physiological signal detector, and said insulin pump, wherein said receiver continuously receives and outputs to a processor said patient physiological signals and said measured patient glucose levels, wherein said processor continuously applies a stacked LSTM (Long Short-Term Memory) Based Deep Recurrent Neural Network to said patient physiological signals and said measured patient glucose levels to predict a patient's predicted blood glucose level and compares said predicted blood glucose level to said measured patient glucose level to calculate a confidence score and actuates an alarm when said confidence score is less than a predetermined threshold level.

2. The method of claim 1 wherein said receiver comprises a personal digital assistant.

3. The method of claim 2 wherein said personal digital assistant further comprises said processor and is a smart phone.

4. The method of claim 1 wherein said patient physiological signal detector is a wearable.

5. The method of claim 4 wherein said wearable is a bracelet or wristband.

6. The method of claim 1 further comprises an activity detector, wherein said activity detector measures data indicating a patients sleep, exercise, eating, and drinking and wherein said activity detector outputs said activity data to said receiver and wherein said processor uses said activity data to verify said confidence score.

7. The method of claim 1 wherein said measured patient glucose levels are preprocessed with Kalman smoothing.

* * * * *